United States Patent [19]

Stotts

[11] Patent Number: 4,913,145
[45] Date of Patent: Apr. 3, 1990

[54] CARDIAC PACEMAKER WITH SWITCHED CAPACITOR AMPLIFIERS

[75] Inventor: Lawrence J. Stotts, Lake Jackson, Tex.

[73] Assignee: Intermedics, Inc., Angleton, Tex.

[21] Appl. No.: 194,174

[22] Filed: May 16, 1988

[51] Int. Cl.[4] ............................................... A61N 1/00
[52] U.S. Cl. ............................................... 128/419 PG
[58] Field of Search ....... 128/419 P, 419 PG, 419 PS, 128/419 PT

[56] References Cited

U.S. PATENT DOCUMENTS

| | | | |
|---|---|---|---|
| 4,585,001 | 4/1986 | Belt | 128/419 PG |
| 4,596,252 | 6/1986 | Nelson | 128/419 PG |
| 4,702,253 | 10/1987 | Nappholz et al. | 128/419 PG |
| 4,768,511 | 9/1988 | DeCote, Jr. | 128/419 PG |
| 4,799,486 | 1/1989 | DuFault | 128/419 PG |
| 4,819,643 | 4/1989 | Menken | 128/419 PG |

Primary Examiner—Francis Jaworski
Assistant Examiner—George Manuel
Attorney, Agent, or Firm—John R. Merkling

[57] ABSTRACT

A cardiac pacemaker has a sense amplifier responsive to signals representative of cardiac activity for passing signal components lying in a selectively variable pass band and for selectively varying the gain of the passed signal. A pair of signal comparators constituting switched capacitor amplifiers, associated with the sense amplifier, are responsive to the filtered and gain adjusted signal for comparison of its magnitude to predetermined target levels for determination of heart rate and the need for change of rate. Two target levels are provided in each comparator for comparison with the level of the detected signal, by multiplexing the switched capacitors. Another switched capacitor amplifier is used to develop a voltage reference level insensitive to temperature, supply voltage, and circuit components, for deriving the target levels for the comparison. Still another multiplexed switched capacitor amplifier comparator is used to develop a first target level to regulate the level of the pacing stimulus, and a second target level for comparison with the supply voltage level of the pacemaker as a measure of the point at which the pacemaker requires replacement.

13 Claims, 4 Drawing Sheets

CARDIAC PACEMAKER WITH SWITCHED CAPACITOR AMPLIFIERS

BACKGROUND OF THE INVENTION

The present invention relates generally to artificial cardiac pacemakers, and more particularly to an implantable bradycardia pacemaker having switched capacitor amplifier circuits for various functions, including sensing of cardiac activity, providing a voltage reference in conjunction with such sensing, and voltage regulation.

In the normal human heart, the sinoartrial (S-A) node is the primary natural pacemaker by which rhythmic electrical excitation is developed. The cardiac impulse generated at the S-A node is transmitted to the atrial chambers at the right and left sides of the heart. In response, the atria contract, pumping blood from those chambers into the respective ventricular chambers. The impulse is transmitted to the ventricles through the atrioventricular (A-V) node, which imposes a delay, and via a conduction system comprising the bundle of His, the right and left bundle branches, and the Purkinje fibers. In response, the ventricles contract, the right ventricle pumping unoxygenated blood through the pulmonary artery to the lungs and the left ventricle pumping oxygenated (arterial) blood through the aorta and the lesser arteries to the body.

The right atrium receives the venous (unoxygenated) blood from the upper part of the body (head, neck and chest) via the superior vena cava, or upper great vein, and from the lower part of the body (abdomen and legs) via the inferior vena cava, or lower great vein. The blood oxygenated by the lungs is carried via the pulmonary veins to the left atrium.

This action is repeated in a rhythmic cardiac cycle in which the atrial and ventricular chambers alternately contract and pump, then relax and fill. One-way valves along the veins, between the atrial and ventricular chambers in the right and left sides of the heart (the tricuspid valve and the mitral valve, respectively), and at the exits of the right and left ventricles (the pulmonary and aortic valves, respectively) prevent backflow of the blood as it moves through the heart and the circulatory system.

The S-A node is spontaneously rhythmic, and the normal cardiac rhythm originating therefrom is termed sinus rhythm. Disruption of the natural pacemaking and propagation system occurs as a result of aging or disease, and is commonly treated by artificial cardiac pacing. The artificial pacemaker is implanted to deliver rhythmic electrical to the heart as necessary to effect stimulation at the desired rate. Bradycardia pacers are designed to sense cardiac activity at a rate lower than the normal sinus rate range, and to return the rate to a selected value within that range. In its simplest form, the pacemaker consists of a pulse generator powered by a self-contained battery pack, and a lead including at least one stimulating electrode electrically connected to the pulse generator. The lead is typically of the catheter type for intravenous insertion to position the stimulating electrode for delivery of electrical impulses to excitable myocardial tissue in the appropriate chamber at the right side of the patient's heart. Usually, the pulse generator is surgically implanted in a subcutaneous pouch in the patient's chest. In operation, the electrical stimuli are delivered to the excitable cardiac tissue via an electrical circuit that includes the stimulating and reference electrodes and the body tissue and fluids.

Typically, the pacemaker is designed to operate in one of three different response modes, namely, asynchronous (fixed rate), inhibited (stimulus generated in absence of specified cardiac activity), or triggered (stimulus delivered in response to specified activity). The demand ventricular pacemaker has been the most widely used type, sensing the patient's natural heart rate and applying stimuli only during periods when the rate falls below the preset pacing rate.

Pacemakers range from the simple fixed rate device that provides pacing with no sensing function, to the highly complex model implemented to provide fully automatic dual chamber pacing and sensing functions. The latter type of pacemaker is the latest in a progression toward physiologic pacing, that is, the mode of artificial pacing that restores cardiac function as much as possible toward natural pacing.

In copending U.S. patent application Ser. No. 07/203/322 of Baker et al., titled "Implantable Cardiac Stimulator with Automatic Gain Control and Bandpass Filtering in Feedback Loop", assigned to the same assignee as is the present application, a cardiac stimulator is disclosed in which the electrical signal representative of detected cardiac activity is subjected to automatic gain control and bandpass filtering. The resulting signal is processed for comparison with inner and outer targets, or reference levels, to determine of the nature of the cardiac activity and ultimately to correct abnormalities in that activity. The device described in the Baker et al. application is primarily concerned with tracking rapidly varying signals of the type commonly associated with fibrillation, in which the heart undergoes random contractions of individual tissue sections rather than coordinated contraction of the entire mass of tissue of the chamber. The device locks in on the signal, changing signal gain as necessary to track the signal, toward delivering a therapy suitable to return the heart to normal cardiac activity. The filtered and amplified signal is compared with inner and outer targets and the gain is varied according to target crossings.

It is a principal object of the present invention to provide a bradycardia pacemaker which utilizes a switched capacitor amplifier and comparator system to sense abnormal cardiac activity and stimulate the heart accordingly.

Another object of the present invention is to provide highly stable voltage reference levels, using switched capacitor amplification, as targets for comparison with the level of the cardiac signal.

Yet another object of the invention is to provide stable regulation of the supply voltage for the pacemaker, utilizing switched capacitor amplification.

SUMMARY OF THE INVENTION

According to the present invention, a pacemaker sense amplifier which differs from the traditional forms is employed to detect evoked potentials. In particular, the sense amplifier comprises a switched capacitor amplifier which allows the amplifier's bandpass frequency and gain to be selectively adjusted, and a dual comparator switched capacitor amplifier system in which each comparator is multiplexed to provide two target reference levels each for comparison against the gain and frequency selected detected signal representative of cardiac activity. If a comparator is tripped as a consequence of the input signal level exceeding the selected target level, the pulse generator of the pacemaker is instructed to pace. On occasions when the target level exceeds the input signal level, the pulse generator is inhibited.

The voltage reference from which the target levels of the comparators are derived also utilizes a switched capacitor amplifier according to the invention. The amplifier is switched in a manner to detect and amplify input levels that are sensitive to temperature in opposite directions such that the sensitivity is cancelled out in the amplification and a subsequent sample and hold operation. The resulting voltage reference level is converted to a reference current which is independent of supply voltage and other circuit components, to further stabilize the output voltage reference.

According to another feature of the invention, a voltage regulator is provided which also employs a multiplexed multi-target single comparator to selectively compare and thereby control the level to which the output pacing capacitors of the pacemaker are charged, and the level selected as the end of service battery voltage of the pacemaker.

BRIEF DESCRIPTION OF THE DRAWINGS

The above and other objects, aspects, features and advantages of the present invention will become more apparent from a consideration of the ensuing detailed description of a presently preferred embodiment thereof, taken together with the accompanying drawings, in which.

DETAILED DESCRIPTION OF THE PREFERRED EMBODIMENT

Figure 1:
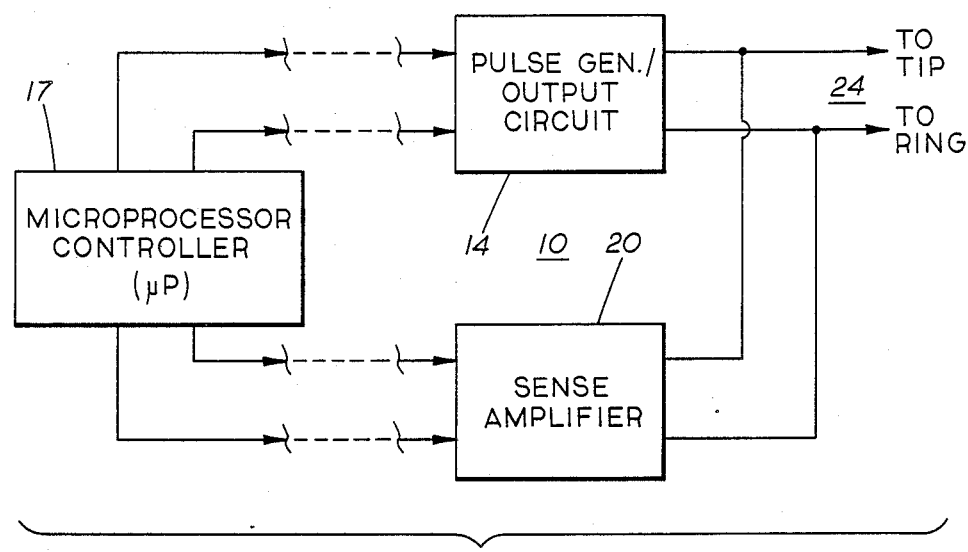
FIG. 1 is a simplifed block diagram of the overall cardiac pacemaker including a microprocessor-controlled sense amplifier according to the invention.

Referring now to FIG. 1, a cardiac pacemaker 10 comprises an output circuit 14, a microprocessor controller 17, and a sense amplifier 20. With bipolar operation, for example, a pair of electrodes may be coupled to output circuit 14 and sense amplifier 20 via a lead assembly 24 for pacing and sensing functions. The output circuit 14 is of any conventional type for generating stimulating pulses which are to selectively delivered (depending on the specific nature of the pacemaker, such as fixed rate, inhibited or triggered) to the heart of the pacemaker patient, via the stimulating cathiodic electrode of lead assembly 24 and through the return path of the body tissue and fluids and the indifferent anodic electrode. Output circuit 14 is also conventionally implemented to be controlled by microprocessor 17. For example, the microprocessor may be used to control the amplitude and width of each stimulating pulse, and the timing the discharge of output capacitors of the output circuit following charging to a desired energy level directly from the pacemaker batteries or from a multiple of the battery output.

Figure 2:
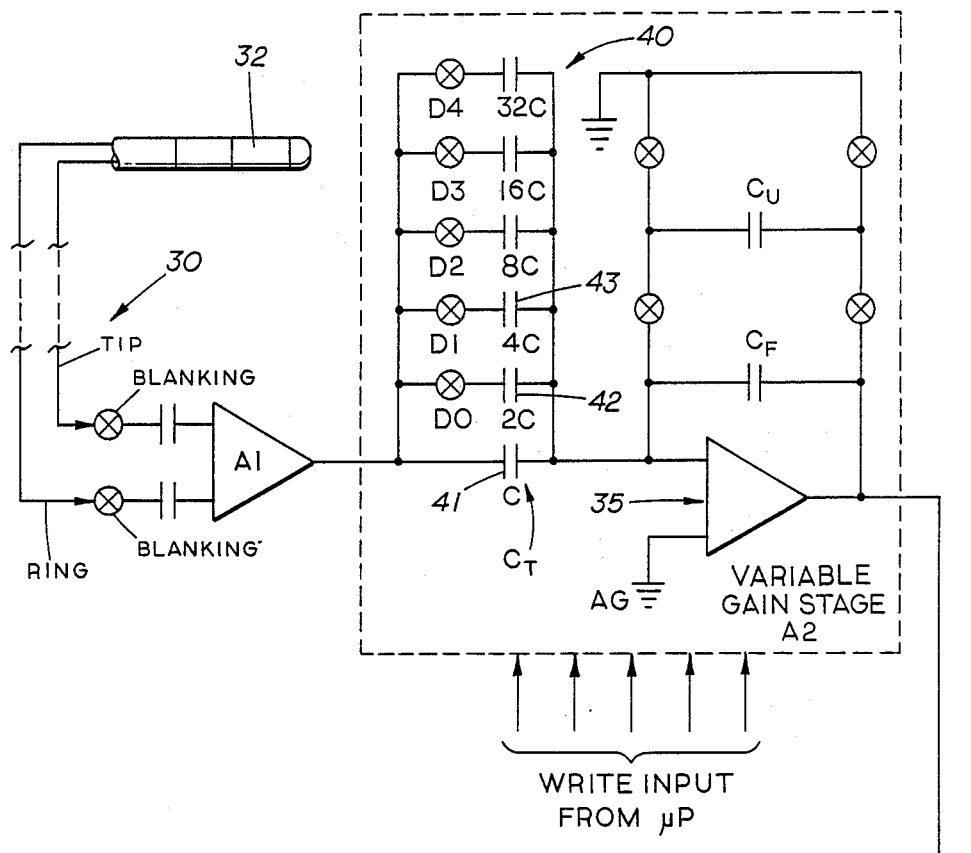
FIG. 2 is a schematic circuit diagram of the preferred embodiment of the sense amplifier of FIG. 1.
Figure 2:
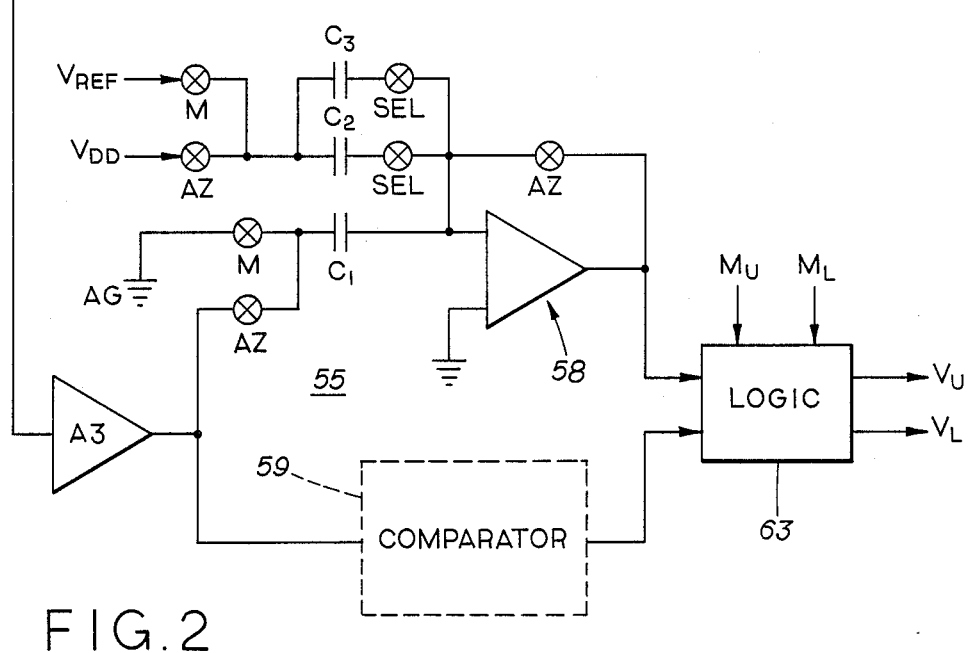

According to the invention, sense amplifier 20, which includes several stages, provides automatic gain control and voltage comparisons by means of switched capacitor amplifiers. The automatic gain control feature of the invention is provided utilizing a low current, low voltage switched capacitor amplifier with good transient response. Referring to FIG. 2, amplifier A1 is a conventional input stage for amplifying and filtering the signal representative of cardiac activity of the patient in whom the pacemaker is implanted. The signal is obtained at the tip and the ring inputs 30 of the implanted pulse generator section which is electrically connected to the sensing electrodes of the pacing lead 32. Blanking switches serve to disconnect the inputs during pace. The output signal of amplifier stage A1 is applied to a variable gain stage A2 comprising a switched capacitor high-pass amplifier 35, and a plurality of switches driven by non-overlapping clock phases. A capacitor CF is connected to a feedback loop for the amplifier. The other capacitor with associated switches is the equivalent circuit of a resistor.

The microcprocessor programs the switches associated with an array 40 of parallel capacitors, for selective electrical connection of capacitors in the array in parallel. The ratio of the capacitors in array 40 is binary weighted, such that capacitor 41 is C, capacitor 42 is 2C, capacitor 43 is 4C, and so forth, the effective capacitance being $C_T$ ($C_{total}$). The flat band gain of the stage is equal to $C_{total}$ over $C_F$ ($C_T/C_F$), which provides gain control. The effect is a variable gain stage which may be written into by the microprocessor to provide the desired capacitance values, and thereby the gain. The output signal of stage A2 is a further filtered and amplified version of the cardiac signal. A subsequent gain, if desired.

Figure 3:
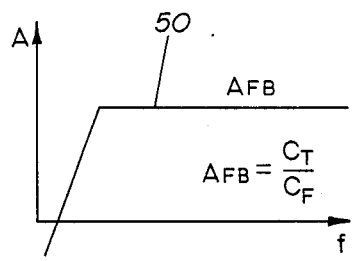
FIG. 3 is a gain-frequency characteristic of the variable gain stage of the circuit of FIG. 2.

The value of unit capacitor $C_U$, adapted to be selectively connected in the feedback path of amplifier 35, is significant in that it aids in determining the gain versus frequency characteristic (FIG. 3) of variable gain stage A2. In particular, the ratio of $C_T$ and $C_F$ together with the unit capacitor $C_U$ and the clock used to set the switches determine the corner 50 of the gain-frequency characteristic. The amplifier stage A2 blocks DC, and at a selected frequency the amplifier provides signal gain. At the high frequencies of the flat band (FB) region of the amplifier, the signal is subjected to a relatively constant gain $A_{FB}$ equal to $C_T/C_F$.

Referring again to FIG. 2, the output signal of A2 (or A3, if used) is fed to a comparator stage 55 which looks at the amplitude of the incoming signal and compares it to a scaled voltage reference. If the amplitude of the incoming signal from the variable gain stage A2 is greater than the level of the voltage reference, the comparator generates a logical output. This indicates that the signal amplitude is sufficiently large and is sensed, and informs the rest of the logic of the action to be taken.

The system of the present invention differs from the AGC/bandpass and comparator system of the cardiac stimulator disclosed in the aforementioned copending Baker et al. application in, among other things, the system by which gain change is effected, comparators are sequenced and targets are created for comparison with the incoming signal. In the present invention the use of switched capacitors allows time division. In particular, in the multi-target dual comparator stage 55, each of two comparators 58 and 59 is multiplexed to provides four targets, or voltage reference levels, with two targets provided by each set of comparators. Comparator 59 is identical to comparator 58, except that the latter is used for establishing and measuring signal voltages and target levels above analog ground whereas the former performs that function below analog ground.

Figure 4:
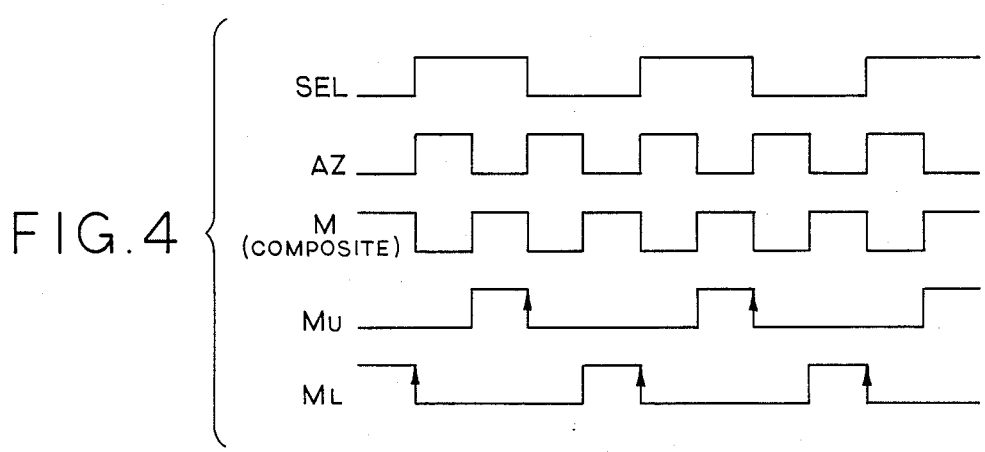
FIG. 4 is a timing diagram for the comparator stage of the amplifier circuit of FIG. 2.

Referring also to the timing diagram of FIG. 4, the basic comparator 58 operates with two phases consisting of an auto-zero (AZ) phase and a measure (M) phase. The phasing for the switches associated with each comparator is indicated by the AX and M labels. In one phase the amplifier is auto-zeroed to charge the capacitors C1 and C2 of comparator 58. Capacitor C2 is connected to $V_{DD}$, and capacitor C1 is connected to the input of the comparator stage. Then, immediately prior to the next phase, the measure phase, those capacitors have been charged such that one is relative to analog ground and the other has the input voltage stored on it away from analog ground. Additionally, they also have the offset voltage of the amplifier stored on them. In the measure phase, capacitor C1 is switched to the analog ground point ($V_{AG}$), and capacitor C2 is switched to $V_{REF}$, and therefore the input signal voltage to the comparator relative to the analog ground point will trip the comparator if that voltage is sufficiently above (or below) analog ground. The comparator stage 55 may be viewed as looking at signal levels above analog ground that have been scaled by the ratio $C1/(C1+C2)$.

In each auto-zero phase, C1 is charged to $V_{in}$ and C2 is connected to $V_{DD}$, as well as to store the offset voltage. In the following phase, C2 is switched to $V_{REF}$ and C1 is switched to $V_{AG}$. If the voltage on C1 does not change, the voltage seen by the comparator would decrease by an amount equivalent to the ratio $C1/(C1+C2)$. If the voltage on C2 does not move, the signal level seen by the comparator would increase. In essence, the comparator is reading $V_{in}$ relative to $V_{DD}$, and $V_{REF}$ relative to $V_{AG}$, and subtracting the two readings. The comparator is utilized to create the zero point and to store all voltage offsets. The $V_{REF}$ to $V_{DD}$ excursion is always the same, and sets a target (in this instance, an inner or lower target) constituting a threshold level based on the ratios of the capacitors (here, C1/C2). When $V_{in}$ is moved up toward $V_{AG}$ in the measure phase, if the voltage at the node being measured returns to become equal to that excursion, the comparator will be tripped.

Figure 5:
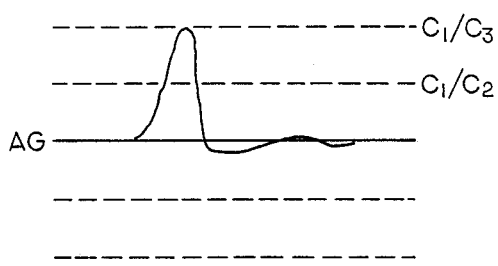
FIG. 5 is a diagram showing the voltage reference targets for an exemplary portion of a cardiac signal.

The upper (or outer) target is established and the input voltage (signal level) is compared against it in a similar manner using capacitor C3 in place of C2. C3 is connected to $V_{DD}$ during the auto-zero phase by the switch selection as shown in the timing diagram, at the same time that C1 is connected to the comparator stage input node. Then, in the following measure phase, C1 is switched to analog ground and C3 is switched to the voltage reference. The upper target is therefore established according to the ratio C1/C3. The relationship of the various voltages and signal levels and the target levels in the comparator stage 55 is shown in FIG. 5.

Referring now to the timing diagram of FIG. 4, there are two phases of the clock, the auto-zero (AZ) phase and the measure (M) phase. The select (SEL) clock selects the phase to provide multiplexing. The M phase actually strobes the value to be latched in at the point indicated on the measure cycle, as shown by the arrows in FIG. 4, to select which target (lower or upper) is to be used as a threshold level at a particular point in the cycle.

In one auto-zero/measure cycle, capacitor C3 is in as a result of the switching produced by the SEL and $M_U$ (M upper) clock. In the next auto-zero/measure cycle, capacitor C3 is out and capacitor C2 is in as a consequence of the switching produced by the SEL and $M_L$ (M lower) clock. The clock designated M in FIG. 4 is merely a composite of the M upper and M lower clocks. The effect is an alternating of the upper and lower targets, with the upper target being latched in during one auto-zero/measure cycle and the lower target being latched in during the next cycle. Hence, a single comparator is multiplexed to provide two different targets.

The target will either be tripped or not, depending on the magnitude of the input signal. Comparator 58 determines the relative magnitudes of the input signal and inner and outer targets above analog ground, and comparator 59 does the same with respect to the input signal and targets below analog ground, as shown in FIG. 5. The two comparators are non-overlapping; that is, both are never high or low at the same time, which is an important aspect of the comparison. One one cycle, the clock signal is applied to a switch such that the amplifier is auto-zeroed. The voltages stored on the capacitors are then measured, and, depending on the magnitude of the stored voltages relative to the reference voltage, the target is either tripped or not. On the next cycle the amplifier is auto-zeroed, the measurement of stored voltage versus voltage reference is taken, and the switch is left open.

It will be observed then, that the capacitor C3 is connected into the circuit on every other cycle. On the cycle that capacitor C3 is in, another target is provided. The same ratio is presented against capacitor C1, but on one phase C3 is in and on the next phase C3 is out. The result is that two different targets are provided, but not at the same time. The sequence is auto-zero, measure, one capacitor; then, auto-zero, measure, second capacitor. In the long term, there are effectively two targets. In reality, the same amplifier is being multiplexed to provide two targets. This is achieved by the addition of capacitor C3 and the associated switch.

The logic circuit 63 includes latches to lock in the information at the end of each measure cycle. A relatively simple OR gating circuit will suffice, with latching based on the application of the M upper and M lower phases of the clock (FIG. 4) coincident with an output from the respective OR gate. The amplifier is auto-zeroed to remove any offset voltage, the capacitors are charged, the amplifier is allowed to settle out, and the information is locked in. By that time this comparator is either right or low, depending upon whether the input voltage to the comparator was sufficiently large to trip the target. At that point in time, the answer is latched in and supplied to the logic circuit. As a consequence of the multiplexing of the two comparators, four targets are provided. The output bits are indicated as $V_U$ (upper) and $V_L$ (lower), and indicate whether an upper target or a lower target was tripped (that is, exceeded by the magnitude of the signal into the dual comparator stage) and, if so, which target specifically. The two targets are scaled two to one in the presently preferred embodiment of the invention, although that is not essential and a different ratio may be used if desired.

Figure 6:
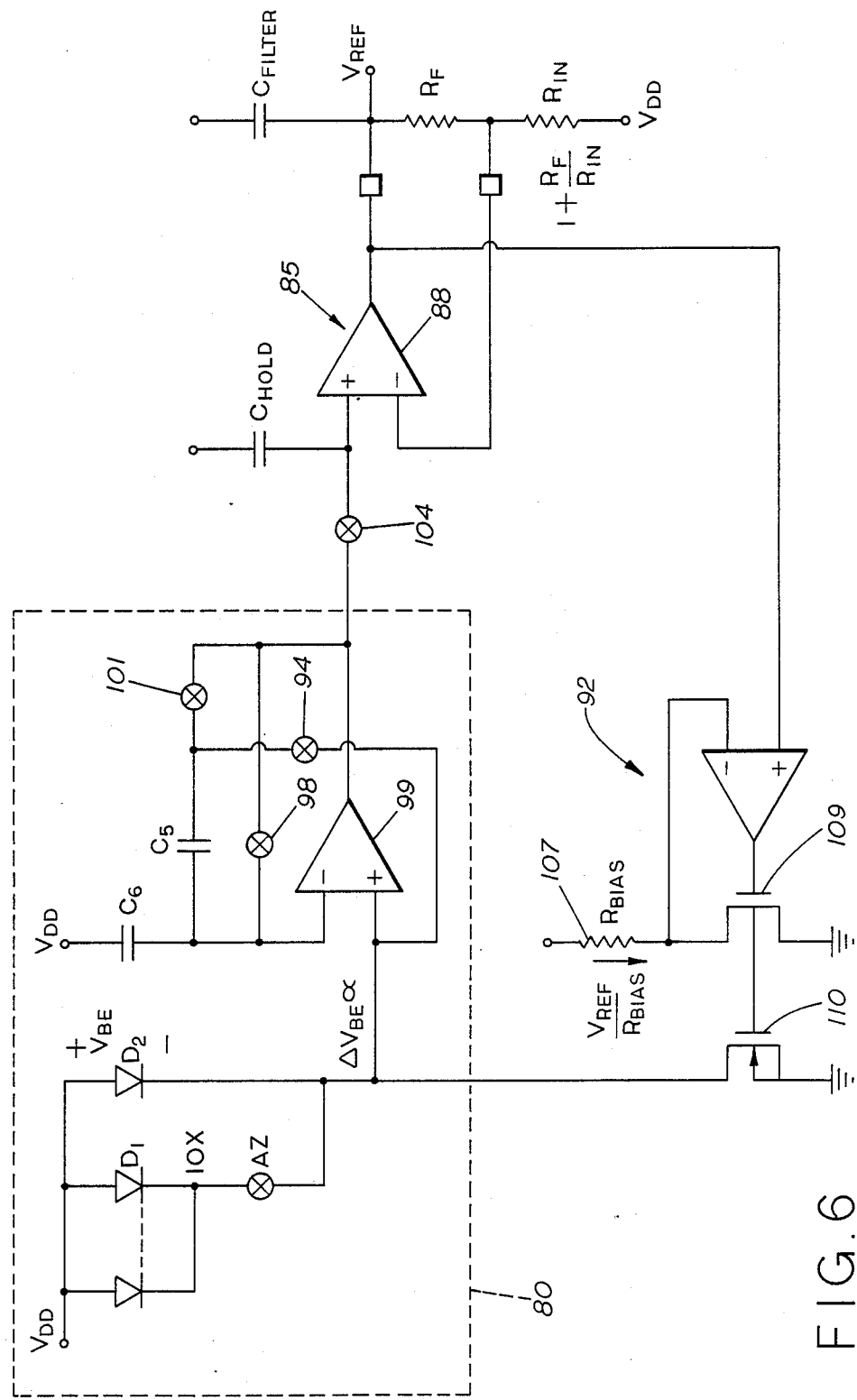
FIG. 6 is a schematic circuit diagram of the preferred embodiment of the invention utilized to provide the voltage reference for the circuit of FIG. 2.

Referring now to FIG. 6, the circuit employed to provide the voltage reference from which the various targets are derived has three main components. The first, in block 80, is a diode array in conjunction with a switch capacitor amplifier having auto-zero and measure phases. Differences in diode voltages are utilized together with the amplifier to create a signal constituting a voltage reference which, at least on first order, is independent of temperature. The second major component is a sample and hold circuit 85 which holds the final result. It ignores the auto-zero phase and provides sample and hold to hold the final answer, and also buffers for outside use. The voltage reference signal is available at the output circuit of the amplifier 88. To make the final answer insensitive to other circuit components to the extent feasible, a current is created from the voltage reference to produce a supply-independent current reference 92 to drive the diodes.

The switched capacitor amplifier is initially in auto-zero mode. Capacitor C5 is thereby connected across the amplifier input (by actuation of switch 94) to store the offset voltage, and thereby putting the amplifier in unity gain. All ten of the diodes D1 are coupled in parallel and are turned on to allow current flow through all of them when switch 96 is on. Each of diodes D1 is of the same emitter size as the other. For any diode, the voltage across it is a function of the current flowing through it. By way of example, the DC value may be approximately 0.5 volt with a given current level. But if two diodes have the same emitter area and the same fixed current flows through them, the total voltage in the previous example will drop by 18 millivolts. This is a function of the emitter size and the current flowing though it—the area of the device. So voltage is a function of the current through the diode and the area of the device.

The ten diodes are identically the same, for ratioing purposes. Instead of making one ten times larger than the other, better ratioing is achieved by using ten identical diodes D1 ratioed to D2. During the auto-zero phase, the voltage produced by the current through diodes D1 and diode D2 is approximately VBE (base-to-emitter) which, for example, may be about half a volt. It should be noted that the diodes are appropriately connected transistors for devices fabricated in CMOS, which is preferred. At this point, however, the amplifier 99 is in the auto-zero phrase also, with switches 94 and 98 closed, and capacitors C5 and C6 are being charged to the offset voltage. Hence, the amplifier 99 does not see VBE as an input voltage.

During the next phase, the measure phase, the auto-zero switches are open and switch 101 is closed to put capacitor C5 back in the feedback circuit of the amplifier, with the offset stored on it. Amplifier 99 is again available to amplify signal appearing at its input, and the amplification will take place according to the ratio of those capacitors, $C_6/C_5$. The incremental input voltage to amplifier 99 is now delta VBE, since diodes D1 have been removed from the current path, and whatever current flow exists is through diode D2. Thus, for example, if the voltage at the input node to the amplifier were 0.5 volt when the large current flowed through the diodes D1 path, the voltage is now considerably less than that (delta VBE), and will be amplified. Consequently, the final voltage is VBE+[(C6/C5)×delta VBE]. That is the answer stored by the example and hold circuit 88 when, at the end of the measure phase, switch 104 is closed.

Voltage VBE obtained with current flow through all of the diodes D1 and D2 decreases with temperature, but delta VBE which is obtained from the ratioed difference in current flow, increases with temperature. The increase of the latter is less than the decrease of the former for any given temperature increase; hence, it is necessary to amplify the differential temperature coefficient to produce a voltage with substantially zero temperature coefficient. In the presently preferred embodiment of the voltage reference circuit, that voltage is the band gap of silicon, and the circuit is essentially a band gap voltage amplifier for providing the voltage reference.

As noted above, it is important that the voltage reference be made independent not only of temperature, but of supply voltage as well. To that end, the voltage $V_{ref}$ resulting from the sample and hold operation is fed back to provide a current reference by means of the circuit 92. The current through resistor 107 ($R_{bias}$) is $V_{ref}/R_{bias}$, which can be ratioed by means of the transistors 109, 110 to control the current flow at the diode array, and provides the desired stability.

Figure 7:
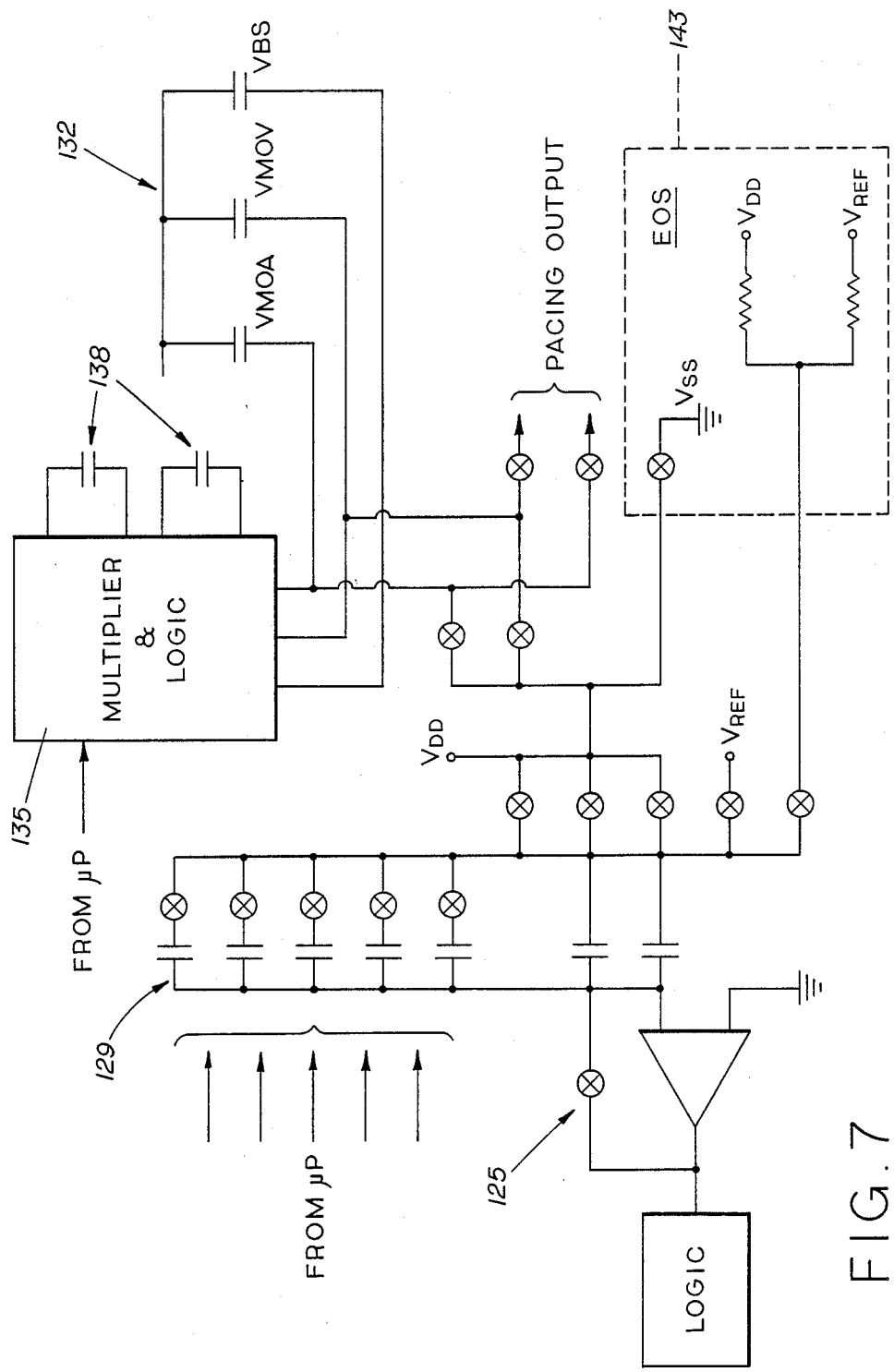
FIG. 7 is a schematic circuit diagram of an exemplary embodiment of a voltage regulator for the pacemaker according to a preferred embodiment of the invention.

Referring now to FIG. 7, a voltage regulator circuit suitable for the sense amplifier comprise a switched capacitor two input comparator 125, which operates in the manner described for a single comparator in the sense amplifier of FIG. 2, except that the comparator of FIG. 7 has five extra capacitors in an array 129 instead of a single capacitor. The capacitors in array 129 are binary weighted to provide 32 different trip points, depending on values that may be programmed in from the microprocessor.

As in the exemplary comparator described with reference to FIG. 2, comparator 125 is multi-target by means of multiplexing. The circuit of FIG. 7 is used in the presently preferred embodiment of the invention to regulate the amplitude of the voltage on the capacitors 132 that supply the pacing outputs to the pacing lead and electrodes. The voltage regulator circuit is also utilized to measure $V_{SS}$ and to compare it to the voltage reference to ascertain when the supply level is at end of service (EOS), or at a point now more often referred to as initial followup indicator (IFI) or elective replacement indicator (ERI). Basically, the indication obtained by virtue of this monitoring and measurement is that the batteries of the pacemaker are sufficiently depleted to require replacement.

The voltage regulator also employs conventional multiplier and logic circuitry with a pair of pumping capacitors 138. This provides DC to DC conversion in which the battery voltage is pumped to a multiple thereof for charging the pacing output capacitors 132. During pacing, the latter capacitors are discharged, and thereafter must be recharged for the next required pace. During that cycle, the logic circuit selects the switching operation of the switches associated with the comparator to allow monitoring by the comparator. When the desired target voltage (determined by comparison with the selected reference voltage) is reached, the comparator is tripped and charging of the output capacitors 132 is ceased.

For the EOS indication, the comparator uses a target voltage appropriate for indicating elective replacement of the pulse generator (the batteries) by the patient's physician. Circuit segment 143 may be laser trimmed for the selected EOS voltage. The capacitor array provides gain control for the comparator so that, depending on the programming of the switches by the microprocessor, a wide array of regulated outputs is available for EOS, as well as for regulation of the charging level of the output capacitors.

Although a preferred embodiment of the invention has been described, it will be apparent to those skilled in the field to which the invention pertains from consideration of the disclosure herein that various changes and modifications may be made to the disclosed embodiment without departing from the true spirit and scope of the invention. Accordingly, it is intended that the invention be limited only to the extent required by the appended claims and applicable rules of law.

What is claimed is:

1. In a cardiac pacemaker,
means for detecting a signal representative of cardiac activity,
means for amplyifying the detected signal,
means responsive to the detected signal for selectively varying the amplification gain thereof, the said gain varying means comprising a plurality of switched capacitors,
means further responsive to the detected signal for passing frequency components of said signal lying in a selectively variable pass band, and
means responsive to the filtered and gain adjusted signal for comparison of a magnitude thereof to predetermined target levels for determination of heart rate, said comparison means including
a pair of signal comparators, and
means for generating at least two target levels for each said comparators, for comparison of the magnitude of the detected signal.

2. The invention of claim 1, wherein said target level generating means comprise a plurality of capacitors and switch means for selectively connecting said capacitors to said signal comparators.

3. The invention of claim 2, further including
microprocessor means for controlling said switch means to selectively vary said target levels.

4. The invention of claim 3 further including
means responsive to said detected signal level exceeding a selected target level for initiating pacing by said pacemaker.

5. The invention of claim 4, further including
means responsive to a selected target level exceeding said detected signal level for inhibiting pacing by said pacemaker.

6. The invention of claim 1, wherein said comparison means further includes
means for establishing a stable voltage reference level for deriving said target levels therefrom.

7. The invention of claim 6, wherein said voltage reference establishing means comprise
means for producing a first input voltage that decreases with temperature,
means for producing a second input voltage that increases with temperature,
switched capacitor amplifier means for combining said first and second input voltages and for producing a temperature insensitive output voltage,
means for sampling and holding the temperature insensitive output voltage of said switched capacitor amplifier means, and
current reference feedback means responsive to the output voltage held by said sample and hold means, for supplying a current to the input of said switched capacitor amplifier means.

8. A voltage reference circuit for a cardiac pacemaker, comprising
means for producing a first input voltage that decreases with temperature,
means for producing a second input voltage that increases with temperature,
switched capacitor amplifier means for combining said first and second input voltages and for producing a temperature insensitive output voltage,
means for sampling and holding the temperature insensitive output voltage of said switched capacitor amplifier means, and
current reference feedback means responsive to the output voltage held by said sample and hold means, for supplying a current to the input of said switched capacitor amplifier means.

9. The invention of claim 8, wherein said pacemaker further includes
means for converting said temperature insensitive output voltage to a plurality of target levels, and
comparator means for comparing a signal representative of cardiac activity to said target levels for controlling the delivery of pacing outputs by said pacemaker.

10. The invention of claim 1, further including
means responsive to the comparison means for providing a pacing stimulus for delivery to the heart, and
further comparator means for developing a target level to regulate the level of the pacing stimulus according, said further comparator means comprising an amplifier with switched capacitor reference means.

11. The invention of claim 10, wherein said further comparator means includes
means for multiplexing the switched capacitors to develop a second target level for comparison with a supply voltage level of said pacemaker as a measure of a condition of the pacemaker related to need to replace the pacemaker.

12. A voltage regulator for a cardiac pacemaker, comprising
a comparator comprising an amplifier and a plurality of selectable capacitors for selectively setting any of a plurality of target voltage levels, said comparator comprising means for comparing a regulable voltage level to a selected target voltage level, and
means responsive to said comparator for adjusting the regulable voltage level to the selected target voltage level.

13. The invention of claim 12 further comprising
means for detecting when an output voltage level of a power source of the pacemaker has fallen below a minimum target level.

* * * * *

REEXAMINATION CERTIFICATE (3318th)

United States Patent [19]
Stotts

[11] B1 4,913,145
[45] Certificate Issued Sep. 9, 1997

[54] CARDIAC PACEMAKER WITH SWITCHED CAPACITOR AMPLIFIERS

[75] Inventor: Lawrence J. Stotts, Lake Jackson, Tex.

[73] Assignee: Intermedics, Inc., Angleton, Tex.

Reexamination Request:
No. 90/004,260, Jun. 10, 1996

Reexamination Certificate for:
| | |
|---|---|
| Patent No.: | 4,913,145 |
| Issued: | Apr. 3, 1990 |
| Appl. No.: | 194,174 |
| Filed: | May 16, 1988 |

[51] Int. Cl.$^6$ ............................................. A61N 1/362
[52] U.S. Cl. ........................... 607/11; 607/12; 607/29
[58] Field of Search ........................... 607/9, 10, 11, 607/12, 14, 15, 17, 18, 27, 28, 29

[56] References Cited

U.S. PATENT DOCUMENTS

| | | | |
|---|---|---|---|
| 3,857,398 | 12/1974 | Rubin | 128/419 |
| 3,976,940 | 8/1976 | Chau et al. | 324/73 R |
| 4,050,004 | 9/1977 | Greatbatch | 363/59 |
| 4,097,766 | 6/1978 | Renirie | 307/229 |
| 4,203,448 | 5/1980 | Keller, Jr. | 128/419 |
| 4,316,472 | 2/1982 | Mirowski et al. | 128/419 |
| 4,321,928 | 3/1982 | Elmquist | 128/419 |
| 4,379,459 | 4/1983 | Stein | 128/419 |
| 4,441,082 | 4/1984 | Hague | 330/129 |
| 4,448,196 | 5/1984 | Money et al. | 128/419 |
| 4,479,266 | 10/1984 | Eumurian et al. | 455/608 |
| 4,494,551 | 1/1985 | Little, III et al. | 128/419 |
| 4,555,668 | 11/1985 | Gregorian et al. | 330/9 |
| 4,633,223 | 12/1986 | Senderowicz | 340/347 |
| 4,649,931 | 3/1987 | Beck | 607/9 |
| 4,665,919 | 5/1987 | Mensink et al. | 128/419 |
| 4,708,144 | 11/1987 | Hamilton et al. | 128/419 |
| 4,726,379 | 2/1988 | Altman et al. | 128/419 |
| 4,803,987 | 2/1989 | Calfee et al. | 128/419 |
| 4,857,778 | 8/1989 | Hague | 307/521 |
| 4,880,004 | 11/1989 | Baker, Jr. et al. | 128/419 |
| 4,969,465 | 11/1990 | Pless et al. | 128/419 |

OTHER PUBLICATIONS

Gregorian R. et al., "Switched–Capacitor Circuit Design," Proceedings of the IEEE, vol. 71, No. 8, Aug. 1983.

Heimer, M., "Analog Signal Processing Circuitry In Implanted Systems," Sessions Presented at Southcon/86, Orlando, Florida, Mar. 18–20, 1986.

Allan, P. et al., "MOS Analog–Digital Converters," Switched Capacitor Circuits, pp. 516–519 (1984).

Redfern, T. et al., "A Monolithic Charge–Balancing Successive Approximation A/D Technique," IEEE Journal of Solid–State Circuits, vol. SC–14, No. 6, Dec. 1979.

Vittoz, E., "Microwatt Switched Capacitor Circuit Design," Electrocomponent Science and Technology, vol. 9, pp. 263–273 (1982).

Gregorian, R. et al., "Programmable Capacitor Arrays," Analog MOS Integrated Circuits For Signal Processing, pp. 417–425 (1986).

(List continued on next page.)

*Primary Examiner*—George Manuel

[57] ABSTRACT

A cardiac pacemaker has a sense amplifier responsive to signals representative of cardiac activity for passing signal components lying in a selectively variable pass band and for selectively varying the gain of the passed signal. A pair of signal comparators constituting switched capacitor amplifiers, associated with the sense amplifier, are responsive to the filtered and gain adjusted signal for comparison for its magnitude to predetermined target levels for determination of heart rate and the need for change of rate. Two target levels are provided in each comparator for comparison with the level of the detected signal, by multiplexing the switched capacitors. Another switched capacitor amplifier is used to develop a voltage reference level insensitive to temperature, supply voltage, and circuit components, for deriving the target levels for the comparison. Still another multiplexed switched capacitor amplifier comparator is used to develop a first target level to regulate the level of the pacing stimulus, and a second target level for comparison with the supply voltage level of the pacemaker as a measure of the point at which the pacemaker requires replacement.

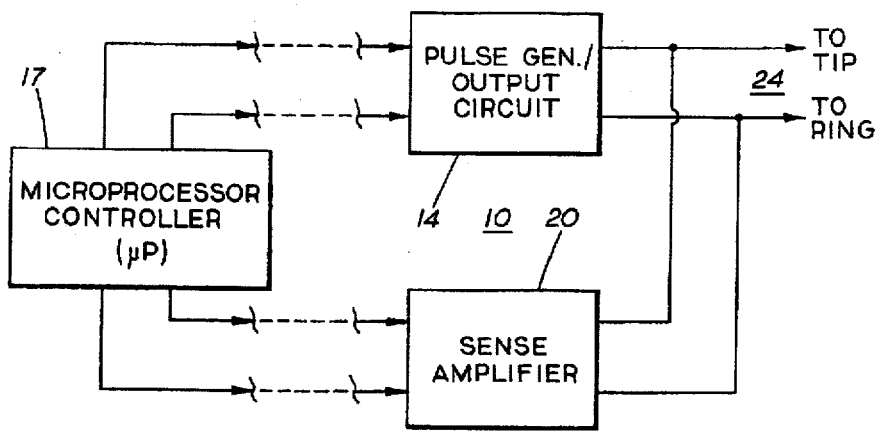

OTHER PUBLICATIONS

David J. Allstot, et al., "An Electrically–Programmable Switched Capacitor Filter," 14 IEEE Journal of Solid–State Circuits 1034–1041, No. 6, (Dec. 1979).

David Bingham, "Analog Circuit Performance Improves with MOS/CMOS Techniques," WESCON/80 Conference Record 1–14 (Sep. 1980).

Robert W. Brodersen, et al., "MOS Switched–Capacitor Filters," 67 Proceedings of the IEEE 61–75, No. 1 (Jan. 1979).

Marc G.R. Degrauwe, et al., "Session XI: Operational Amplifiers and Voltage Regulators," IEEE International Solid–State Circuits Conference 142, 143, 326 (Feb. 1985).

Olivier Y. De Vel, "R–Wave Detection in the Presence of Muscle Artifacts," 31 IEEE Transactions on Biomedical Engineering 715–717, No. 11 (Nov. 1984).

Paul R. Gray, et al., "Analog–Digital Conversion Techniques For Telecommunications Applications," reprinted in Design of MOS VLSI Circuits For Telecommunications 212–235 (Yannis Tsividis and Paolo Antognetti eds., 1985).

Roubik Gregorian, et al., "A Single Chip Speech Synthesizer Using a Switched–Capacitor Multiplier," 18 IEEE Journal of Solid–State Circuits 65–75, No. 1 (Feb. 1983).

David A. Hodges, et al. "Potential of MOS Technologies for Analog Integrated Circuits," 13 IEEE Journal of Solid–State Circuits 285–294, No. 3 (Jun. 1978).

John L. Hood, "LM109 three–terminal voltage regulator," Wireless World 41–44 (Mar. 1982).

Bedrich J. Hosticka, et al., "Real–Time Programmable Low Power SC Bandpass Filter," 17 IEEE Journal of Solid–State Circuits 499–506, No. 3 (Jun. 1982).

B. J. Hosticka, "Nonlinear Analog MOS Circuits," reprinted in Design of MOS VLSI Circuits For Telecommunications 372–428 (Yannis Tsividis and Paolo Antognetti eds., 1985).

James B. Kuo, et al., "MOS Pass Transistor Turn–Off Transient Analysis," 33 IEEE Transactions on Electron Devices 1545–1555, No. 10 (Oct. 1986).

Robert H. McCharles, et al., "Charge Circuits for Analog LSI," 25 IEEE Transactions on Circuits and Systems 74–81, No. 7 (Jul. 1978), reprinted in 25 IEEE Transactions on Circuits and Systems 490–497 (Jul. 1978).

James L. McCreary, et al., "All–MOS Charge Redistribution Analog–to–Digital Conversion Techniques" (Part I, Part II), 10 IEEE Journal of Solid–State Circuits 371–385, No. 6 (Dec. 1975).

John Michejda, et al., "A Precision CMOS Bandgap Reference," 19 IEEE Journal of Solid–State Circuits 1014–1021, No. 6, (Dec. 1984).

Willy M.C. Sansen, "On the Integration of an Internal Human Conditioning System" 17 IEEE Journal of Solid–State Circuits 513–521, No. 3 (Jun. 1982).

Band–Sup Song, et al., "A Precision Curvature–Compensated CMOS Bandgap Reference," 18 IEEE Journal of Solid–State Circuits 634–643, No. 6 (Dec. 1983).

Yannis P. Tsividis, et al., "A CMOS Voltage Reference," 13 IEEE Journal of Solid–State Circuits 774–778, No. 6 (Dec. 1978).

Eric A. Vittoz, et al., "A Low–Voltage CMOS Bandgap Reference," 14 IEEE Journal of Solid–State Circuits 573–577, No. 3 (Jun. 1979).

Bertram J. White, et al., "A Monolithic Dual Tone Multifrequency Receiver," 14 IEEE Journal of Solid–State Circuits 991–997, No. 6 (Dec. 1979).

Robert J. Widlar, "Local IC Regulator for Logic Circuits," Computer Design 115–120 (1971).

Yen S. Yee, et al., "A 1 mV MOS Comparator," 13 IEEE Journal of Solid–State Circuits 294–297, No. 3 (Jun. 1978).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

THE DRAWING FIGURES HAVE BEEN CHANGED AS FOLLOWS:

Polarities added to the amplifier in FIG. 6.
Capacitors labeled and line added in FIG. 7.

AS A RESULT OF REEXAMINATION, IT HAS BEEN DETERMINED THAT:

The patentability of claims 1-9, 12-13 are confirmed.

Claim 10 is determined to be patentable as amended.

Claim 11, 23 dependent on an amended claim, is determined to be patentable.

New claims 14-23 are added and determined to be patentable.

10. The invention of claim 1, further including
means responsive to the comparison means for providing a pacing stimulus for delivery to the heart, and
further comparator means for developing a target level to regulate the level of the pacing stimulus [according] *accordingly*, said further comparator means comprising an amplifier with switched capacitor reference means.

*14. The invention of claim 1, further including means responsive to the comparison means for providing a pacing stimulus for delivery to the heart, and further comparator means for developing a target level to regulate the level of the pacing stimulus.*

*15. The invention of claim 1, further including means responsive to the comparison means for providing a pacing stimulus for delivery to the heart, and further comparator means comprising an amplifier with switched capacitor reference means.*

*16. The voltage regulator of claim 12 wherein said plurality of selectable capacitors comprises a binary weighted bank of selectable capacitors.*

*17. A cardiac pacemaker comprising the voltage regulator of claim 12, and further comprising an output capacitor that stores the regulable voltage.*

*18. The cardiac pacemaker of claim 17 further comprising a pumping capacitor for charging said output capacitor.*

*19. A cardiac pacemaker comprising the voltage regulator of claim 12, and further comprising a microprocessor which selects at least one capacitor of said plurality of selectable capacitors to set the selected target voltage level.*

*20. A cardiac pacemaker comprising the voltage regulator of claim 12, and further comprising a switched capacitor reference means.*

*21. A cardiac pacemaker comprising the voltage regulator of claim 12, and further comprising means for comparing a plurality of regulable voltage levels to one or more selected target voltage levels, and means for selectively connecting each of said regulable voltage levels to the voltage regulator for regulation by the voltage regulator.*

*22. The cardiac pacemaker of claim 21, further comprising a switch for selectively connecting one of said plurality of regulable voltage levels to the voltage regulator for regulation by the voltage regulator.*

*23. The voltage regulator of claim 12, wherein at least one of said plurality of selectable capacitors has an input terminal that is switchably connected to a first voltage source during a first time phase, and is switchably connected to a second voltage source during a second time phase, said first and second time phases being non-overlapping in time.*

* * * * *